United States Patent [19]

Johnson et al.

[11] Patent Number: 5,532,771
[45] Date of Patent: Jul. 2, 1996

[54] EYE FUNDUS OPTICAL SCANNER SYSTEM AND METHOD

[75] Inventors: Joel C. Johnson, Lake Oswego; Robert B. Hill, Portland, both of Oreg.

[73] Assignee: EDI of Louisiana, Inc., Baton Rouge, La.

[21] Appl. No.: 169,494

[22] Filed: Dec. 17, 1993

[51] Int. Cl.[6] .............................. A61B 3/10; G02B 26/08
[52] U.S. Cl. ........................... 351/211; 351/205; 359/205
[58] Field of Search ..................................... 351/221, 211, 351/214, 205, 217; 359/821, 198, 205, 210, 19

[56] References Cited

U.S. PATENT DOCUMENTS

| | | | |
|---|---|---|---|
| 4,109,237 | 8/1978 | Hill | 340/146.3 |
| 4,135,791 | 1/1979 | Govignon | 341/7 |
| 4,393,366 | 7/1983 | Hill | 382/2 |
| 4,620,318 | 10/1986 | Hill | 382/2 |
| 4,764,005 | 8/1988 | Webb | 351/221 |
| 4,768,873 | 9/1988 | Webb | 351/221 |
| 4,786,142 | 11/1988 | Karecki | 350/319 |
| 4,923,297 | 5/1990 | Arndt | 351/208 |
| 5,161,040 | 11/1992 | Yokoyama et al. | 359/19 |

Primary Examiner—William L. Sikes
Assistant Examiner—Hung Xuan Dang
Attorney, Agent, or Firm—Stoel Rives

[57] ABSTRACT

An optical scanner (100) includes a rotating scanner disk (116) that integrates a multifocal Fresnel fixation lens (114), a Fresnel optical scanner (122, 124), and an angular position encoder (140) into a unitary, inherently aligned, compression-molded component. An individual being identified views through the multifocal Fresnel fixation lens an image of a pinhole (108) illuminated by a light source (104). The multifocal lens is centered on the disk and creates multiple in- and out-of-focus images (180, 182, 184, 186) of the pinhole image. The combined image appears to the individual as a set of circular images (190, 192, 194, 196), one of which is in focus. The images appear concentric when the individual is properly aligned with the disk and associated optics. The Fresnel optical scanner receives IR light from the light source and creates an IR scanning beam (126) when the disk is rotated. IR light reflected by the fundus (12) of the individual returns via a reciprocal path, by way of a beam splitter (112), and into a detector (134) to generate image data. The disk integrates and inherently aligns multiple optical elements, resulting in a 60 percent reduction of optical components relative to prior scanners.

59 Claims, 4 Drawing Sheets

EYE FUNDUS OPTICAL SCANNER SYSTEM AND METHOD

TECHNICAL FIELD

This invention relates to optical scanning systems and more particularly to an apparatus and a method for scanning the fundus of the eye of an individual to obtain by ocular reflection an identification pattern unique to the individual.

BACKGROUND OF THE INVENTION

There are previously known apparatus and methods for identifying individuals by scanning their retinal vasculature patterns. U.S. Pat. No. 4,109,237, issued Aug. 22, 1978, and U.S. Pat. No. 4,393,366, issued Jul. 12, 1983 describe using a rotating optical scanning beam to obtain an identification pattern from the fundus of the eye. The earlier scanner employed green light for the scanning beam, whereas the later, improved, scanner employed infrared ("IR") radiation to detect the vasculature of the choroid of the eye. The choroidal vasculature forms a matting behind the retina, including the area of the macula and fovea where retinal blood vessels are very small or nonexistent. The blood vessels of the choroid are stable, as are those of the retina, and thus may be used for obtaining data relating to the identity of an individual. However, because the scanners obtain data from a annular region centered around the optic nerve, the resulting identification pattern is very sensitive to head tilt.

U.S. Pat. No. 4,620,318, issued Oct. 28, 1986 describes an improved apparatus and method for identifying individuals through the ocular light reflection pattern from the fundus of the eye. A fixation beam is provided along the visual axis of the eye, and a scanner obtains an identification pattern from a substantially annular scanning pattern centered around the fovea. As described above, scanning with IR light provides reflections from the vasculature of the choroid as well as the vasculature of the retina. The annular scan centered about the visual axis, and therefore on the fovea, provides substantially identical identification patterns from a given individual regardless of a head tilt angle relative to the visual axis.

Figure 1:
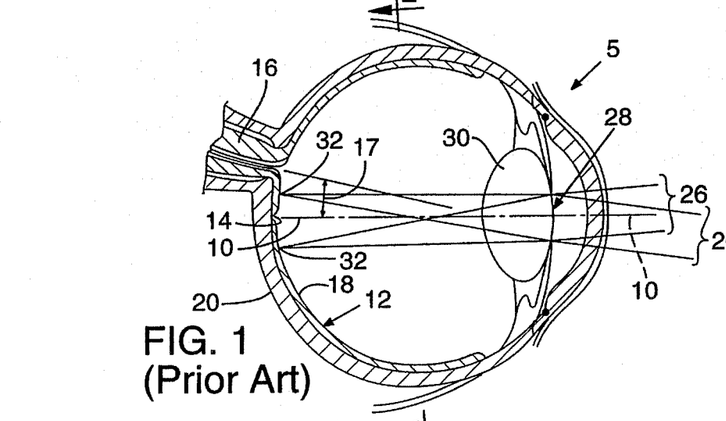
FIG. 1 is a cross-sectional side view of a human eye showing major structures of the eye and ray trace lines representing paths followed by a prior art fundus scanning beam.
Figure 2:
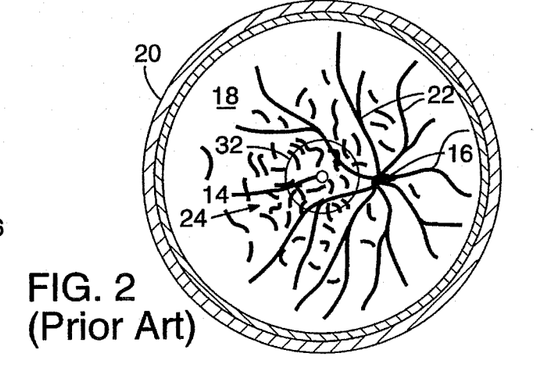
FIG. 2 is a sectional view taken along lines 2—2 of FIG. 1.

FIGS. 1 and 2 show an eye 5 into which the fixation and scanner beams are projected. Eye 5 is centered on visual axis 10 that intersects a fundus 12 at a fovea 14. An optic nerve 16 is located at an angle 17 approximately 15.5 degrees off visual axis 10. Fundus 12 includes a retina 18 and a choroid 20.

FIG. 2 shows an exemplary retinal vasculature 22 branching from the area of optic nerve 16. Retinal vasculature 22 is readily apparent upon observation with either visible or IR radiation. However, when illuminated with IR radiation, the vasculature of choroid 20 also becomes observable as is depicted by the matting of choroidal vessels 24. Choroidal vessels 24 are apparent in the area of fovea 14.

With reference to FIGS. 1 and 2, a collimated IR scanning beam 26 reflects from a combination of retinal vasculature 22, choroidal vessels 24, and various other structures and pigmentation. IR scanning beam 26 enters a pupil 28 of eye 5 and is focused on fundus 12 by a lens 30. IR scanning beam 26 traverses a circular locus of points 32 that are substantially centered around fovea 14.

Figure 3:
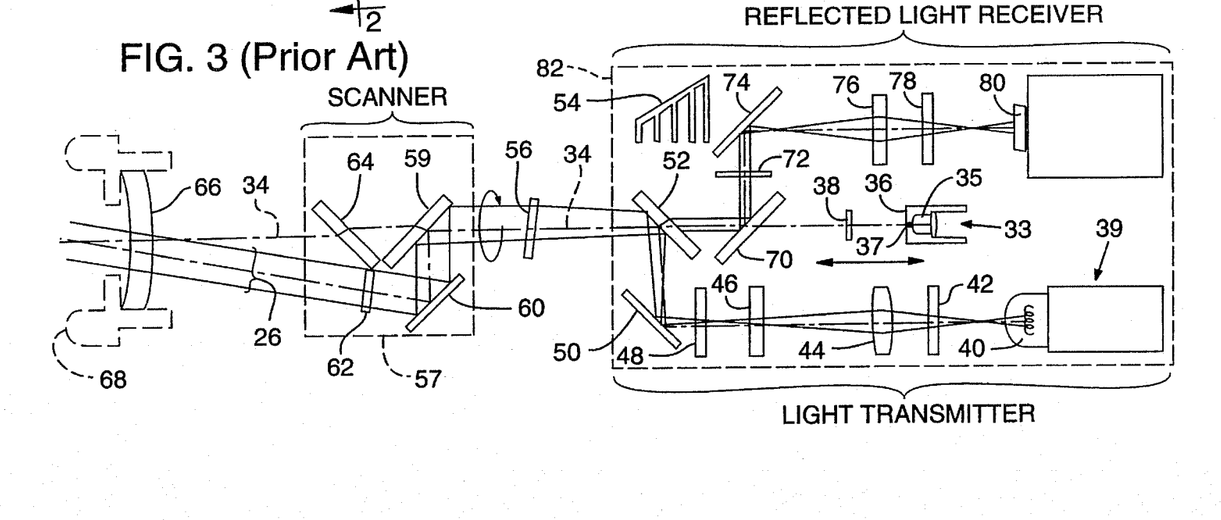
FIG. 3 is a simplified pictorial plan view of a prior art fundus scanning system, including its major optical components and associated ray trace lines.

The prior art scanning apparatus designed to achieve the above-described result is shown in FIG. 3. A fixation target 33 allows an individual to properly focus eye 5 and align its visual axis 10 with an optical axis 34 of the scanning apparatus. Fixation target 33 includes a visible light-emitting diode 35 positioned in a mounting structure 36 having a pinhole 37. Light-emitting diode 35 illuminates a fixation reticle 38 formed by a plate having multiple concentric circles upon which eye 5 is focused.

An IR source 39 provides a beam of IR radiation for scanning fundus 12 of eye 5. IR source 39 includes an incandescent tungsten bulb 40 that produces light that passes through a spatial filter 42 and is refracted by a lens 44. An IR filter 46 passes only the IR wavelength portion of the beam, which then passes through a pinhole 48. The beam is then reflected by a mirror 50 onto a beam splitter 52 that is mounted to coincide with the fixation target optics and optical axis 34.

A portion of radiation emanating from IR source 39 is transmitted through beam splitter 52 and is absorbed in a light trap 54. The remaining radiation is reflected along optical axis 34 to an objective lens 56, which collimates and directs the beam along optical axis 34.

A scanner is provided for directing the beam into the fixated eye from a plurality of sequential, angularly divergent positions. The scanner includes a rotatable housing 57 and scanner optics that rotate with the housing as indicated by a circular arrow 58.

The scanner optics include a hot mirror 59 (one that reflects IR radiation while passing visible light), located in the path of the source beam and the fixation beam. The visible wavelength fixation beam is passed through hot mirror 59, while the IR source beam is reflected away from optical axis 34. A scanner mirror 60 is positioned in housing 57 at a point spaced apart from optical axis 34 and is oriented to direct the IR beam through an IR filter 62 and into eye 5 as housing 57 rotates. Hot mirror 59 causes a displacement of the fixation beam, so an offset plate 64 is positioned to compensate for the displacement.

An objective lens 66 is mounted in an eyepiece 68 to collimate and direct the beam into eye 5. Placing objective lens 66 at this location provides simplified focusing of the device for individuals with other than 20/20 vision.

When housing 57 rotates, the IR beam is directed into eye 5 in an annular scanning pattern centered on the fovea as represented by circular locus of points 32 (FIG. 2). Light reflected from fundus 12 of eye 5 varies in intensity depending on the structures encountered by the scan. The reflected light is recollimated by lens 30 of eye 5, directed out pupil 28, back through objective lens 66 and IR filter 62, and reflected off scanner mirror 60 and hot mirror 59. The reflected beam is then focused by objective lens 56 onto beam splitter 52 which passes a portion of the reflected scanning beam to a hot mirror 70 that reflects the beam through a spatial filter 72. The beam is next reflected by a mirror 74, refracted by a lens 76, and passed through another spatial filter 78 to a detector 80.

Fixation target 33, IR source 39, detector 80, and associated optical components are mounted on a carriage 82. The above-described beams enter and leave carriage 82 coincidentally and focus at optically equal distances from eye 5. Longitudinal movement of carriage 82 serves to focus the device for individuals with other than 20/20 vision. Therefore, when an individual moves carriage 82 longitudinally to focus on fixation target 33, the optics associated with IR source 39 and detector 80 are simultaneously focused. Fixation mounting structure 36 and pinhole 37 are positionable on carriage 82 to provide fine alignment of fixation target 33 and fixation reticle 38 with optical axis 34.

IR source 39 has a fixed intensity, but fixation target 33 has an adjustable intensity by which an individual can optimize the viewability of fixation target 33 through fixation reticle 38. However, changing the intensity of fixation target 33 causes the diameter of pupil 28 to change which can cause variations in the signal received by detector 80. Moreover, individuals are sometimes confused by the image created by fixation target 33 and fixation reticle 38, causing them to improperly align visual axis 10 with optical axis 34.

Other problems with the prior art device of FIG. 3 include difficulty maintaining alignment of the multiple optical components, lack of identification repeatability caused by manual focusing and the confusing fixation target, and expense associated with the optical complexity.

What is needed, therefore, is a substantially simplified optical scanner system having inherent optical alignment, no need for manual focusing, and an improved fixation target.

SUMMARY OF THE INVENTION

An object of this invention is, therefore, to provide a fundus scanning apparatus and method having inherently aligned optics.

Another object of this invention is to provide a fundus scanning apparatus and a method in which the optics do not require manual focusing to adapt to a wide range of human visual acuities.

A further object of this invention is to provide a fundus scanning apparatus and a method in which the optics have substantially reduced complexity.

Still another object of this invention is to provide a fundus scanning apparatus and method having substantially improved data repeatability.

Accordingly, this invention provides a simplified and improved optical scanner system including a single fixation and IR scanning source; a beam splitter; a detector; and a rotating scanner disk that integrates a multifocal fixation lens, an optical scanner, and an annular position encoder into a single, inherently aligned, molded component.

An individual being identified views an image of a fixation source pinhole through the multifocal Fresnel fixation lens. The multifocal lens is centered on the disk and creates multiple in- and out-of-focus images of the fixation target image. The combined image appears as a set of circular images, one of which is in focus. The images appear concentric when the individual is properly aligned with the disk and associated optics.

An aspheric Fresnel lens and a Fresnel prism form the optical scanner, which is positioned adjacent to the periphery of the disk. The optical scanner receives IR light from the source and creates an IR scanning beam when the disk is rotated. IR light reflected by the fundus of the individual returns along a reciprocal path, through the beam splitter, and into the detector. The detector generates image data in response to reflected IR intensity variations resulting from vascular structures that occupy an annular region scanned on the fundus. A position encoder molded into the disk correlates the image data to the angular position of the Fresnel prism.

The disk integrates and inherently aligns multiple optical elements into a single molded component, resulting in a 60 percent reduction in the number of optical components typically found in prior scanners. Most remaining optical components are of simpler design than that of optical components found in prior scanners, thereby providing a substantially simpler, more stable, and repeatable optical identification scanner.

Additional objects and advantages of this invention will be apparent from the following detailed description of preferred embodiments thereof that proceeds with reference to the accompanying drawings.

DETAILED DESCRIPTION OF PREFERRED EMBODIMENTS

Figure 4:
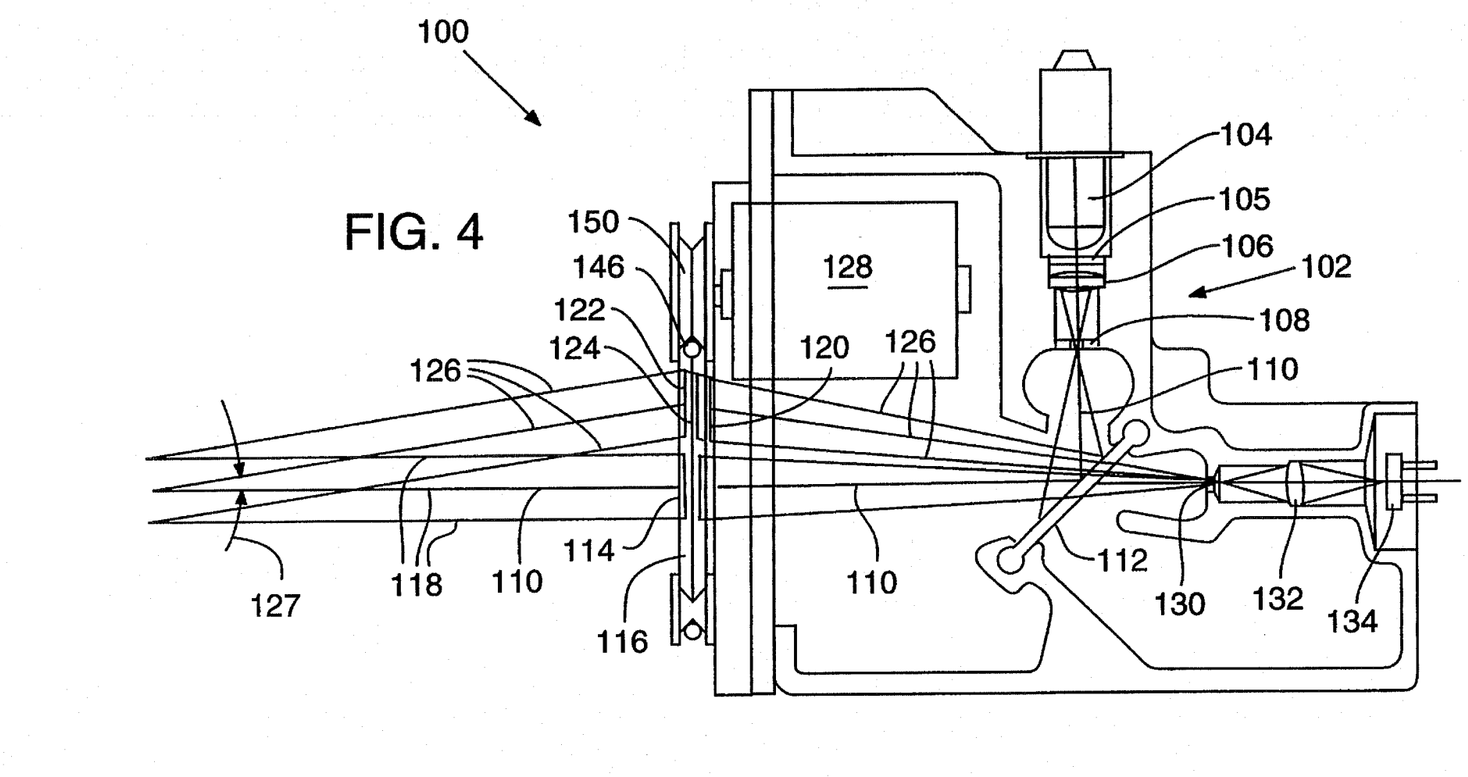
FIG. 4 is a simplified pictorial plan view of a preferred embodiment of a fundus scanning system of the invention, including its major optical components and associated ray trace lines.

FIG. 4 shows a preferred embodiment of an optical scanner system 100 according to this invention. A fixation target (shown generally at 102) includes an illumination source 104, a diffuser 105, a condenser lens 106, and a 1.6 millimeter diameter pinhole 108. Source 104, a 3.5 watt, Krypton-type, center-filament bulb; diffuser 105, a Corning lenticular "fly eye" lens; and condenser lens 106 together provide adequate illumination of pinhole 108. Source 104 provides a spectrum and intensity of radiation sufficient to function as an IR scanning source in addition to illuminating fixation target 102, thereby eliminating the requirement for separate prior art IR source 39 (FIG. 3) and its associated optical components 40, 42, 44, 46, 48, 50, and 52.

Visible light travels from fixation target 102 generally along an optical axis 110, reflects off a beam splitter 112, and through a multifocal fixation lens 114 (described in detail later) that is mounted at the center of a scanner disk 116. Multifocal fixation lens 114 generally collimates fixation rays 118 that originate at illuminated pinhole 108 and terminate in the eye of the individual being scanned.

IR light travels from fixation target 102, generally along optical axis 110, reflects off beam splitter 112, through an IR filter 120, to a Fresnel prism 122 and a aspheric Fresnel lens 124 (both described in detail later). IR filter 120, Fresnel prism 122, and aspheric Fresnel lens 124 share a common axis that is offset from the center of scanner disk 116. Fresnel prism 122 and aspheric Fresnel lens 124 generally deflect and collimate IR scanning rays 126 that originate at illuminated pinhole 108, travel the above-described path, and reflect off the fundus of the individual being scanned. Scanning rays 126 are deflected at about a 10 degree angle 127 relative to optical axis 110; and when scanner disk 116 is rotated by a motor 128, scanning rays 126 scan a 0.39 millimeter wide annular path centered around the fovea of the individual being scanned.

Reflected IR scanning rays 126 return to optical scanner system 100 along a reciprocal path through Fresnel prism 122, aspheric Fresnel lens 124, and IR filter 120 to beam splitter 112. A portion of the reflected IR scanning rays 126 are transmitted through beam splitter 112 to an IR detector that includes a 2.5 millimeter pinhole 130, a condenser lens 132, and a silicon photodiode 134. The relatively simple optical path of the IR detector eliminates the requirement for optical components 74 and 78 associated with prior art detector 80 (FIG. 3).

Figure 5:
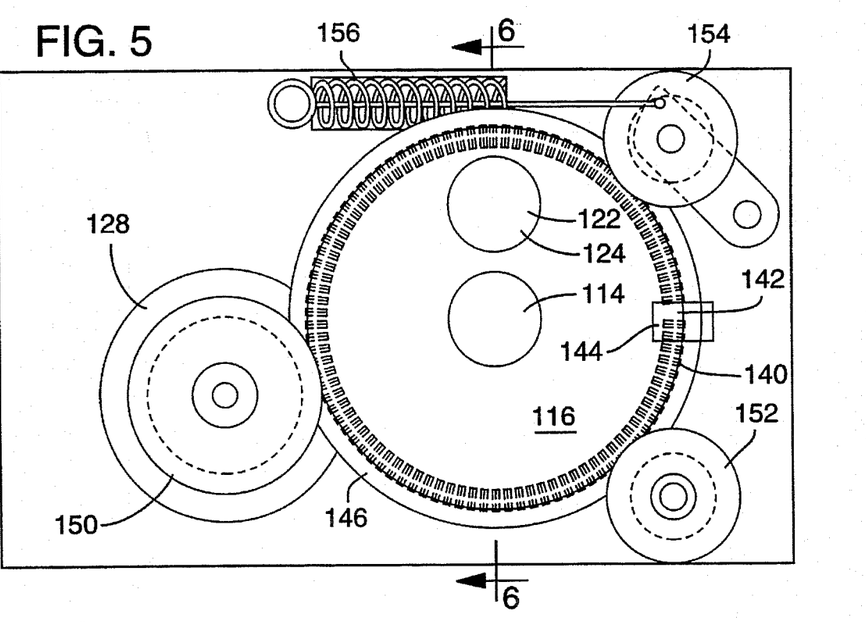
FIG. 5 is an enlarged frontal elevation view of a scanner disk according to this invention showing the spatial relationship of a fixation lens, an optical scanner, a disk rotation motor, disk mounting bearings, and a disk angular position encoder.

FIG. 5 shows a frontal view of scanner disk 116 with its associated multifocal fixation lens 114, Fresnel prism 122, and aspheric Fresnel lens 124. Fresnel prism 122 and aspheric Fresnel lens 124 are formed as integral parts of scanner disk 116 with their major surfaces positioned in opposed, plane parallel relation. Scanner disk 116 is preferably compression-molded from a transparent acrylic plastic material having an index of refraction of 1.484 at a radiation wavelength of 900 nanometers. Another molding process, such as injection molding may be employed. Also molded into the periphery of scanner disk 116 are 96-1 equally spaced apart encoder bumps 140. An indexing angle for scanner disk 116 is indicated by a missing one of bumps 140 at a location 142. A reflection-sensing photo-optical sensor 144 is mounted adjacent to scanner disk 116 to detect encoder bumps 140. The surface of scanner disk 116 reflects light from photo-optical sensor 144; whereas encoder bumps 140 act as lenses that disperse light. As scanner disk 116 rotates, the alternating light reflection and dispersion is detected by photo-optical sensor 144 and converted to rotational angle information for scanner disk 116 by conventional means.

Figure 6:
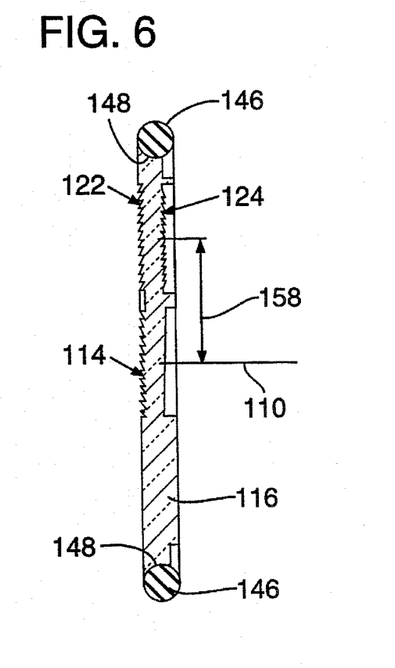
FIG. 6 is a sectional view taken along line 6—6 of FIG. 5 showing the scanner disk, multifocal fixation lens, a Fresnel prism, and an aspheric Fresnel lens.

FIG. 6 shows an O-ring 146 that encircles a rim 148 that is molded into the periphery of scanner disk Referring again to FIG. 5, O-ring 146 frictionally engages a grooved capstan 150 on motor 128 that is configured to rotate scanner disk 116 at about six revolutions per second. Scanner disk 116 is suspended between grooved capstan 150 and grooved bearings 152 and 154 that are generally spaced as shown around the periphery of scanner disk 116.

Grooved bearing 154 is biased toward scanner disk 116 by a spring 156 having a nominal 440 gram force. Moving grooved bearing 154 away from scanner disk allows simple installation and removal of scanner disk from optical scanner system 100.

FIG. 6 is a sectional view of scanner disk 116 taken along lines 6—6 of FIG. 5 to show the relative positions of aspheric Fresnel lens 124, Fresnel prism 122, and multifocal fixation lens 114, all of which are preferably made using Fresnel techniques.

A conventional Fresnel lens can be described as a single focal-length lens having a thickness that is minimized by producing the required focal length-producing contour in radially stepped increments. The radial width of each increment is constant, but the thickness change between each increment varies across the face of the lens by the amount necessary to produce the requisite focal length.

Aspheric Fresnel lens 124 is a conventional Fresnel lens having a 72 millimeter effective focal length. Aspheric Fresnel lens 124 and Fresnel prism 122 face one another, and their centers are offset from optical axis 110 of scanner disk 116 by a distance 158 of 11.2 millimeters.

A Fresnel prism can be described as a prism having a thickness that is minimized by producing the required prism angle in linearly stepped increments. The width of each linear increment is constant, and the required prism angle is repeated across the face of the Fresnel prism.

Figure 7:
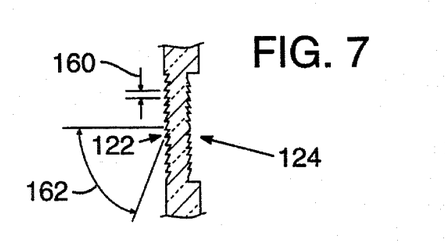
FIG. 7 is an enlarged fragmentary view showing details of the Fresnel prism and aspheric Fresnel lens shown in FIG. 6.

Cross-sectional details of Fresnel prism 122 and aspheric Fresnel lens 124 are shown enlarged in FIG. 7. A linear increment 160 of 0.125 millimeter and a prism angle 162 of 70.238 degrees is repeated across the face of Fresnel prism 122. Aspheric Fresnel lens 124 has a 34.6 millimeter base curvature, a −1.6698 conic constant, and a 0.125 millimeter radial increment.

Figure 8:
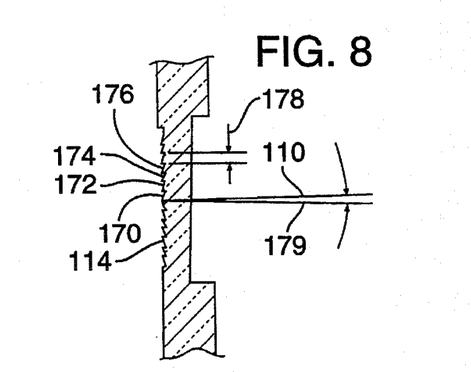
FIG. 8 is an enlarged fragmentary view showing multifocal Fresnel lens details of the fixation lens shown in FIG. 6.

Cross-sectional details of multifocal fixation lens 114 are shown enlarged in FIG. 8. Multifocal fixation lens 114 differs from a conventional Fresnel lens because each successive radial step has a contour defining a different focal length. The number of different focal lengths employed and the radial ordering of the resulting focal-length pattern is relatively unimportant.

The preferred pattern employs four different focal-length contours chosen to accommodate a wide range of human visual acuity. Starting at optical axis 110 and progressing radially outward on multifocal fixation lens 114, a first contour 170 has an effective focal length of 70.5 millimeters, a second contour 172 has an effective focal length of 72 millimeters, a third contour 174 has an effective focal length of 74.4 millimeters, and a fourth contour 176 has an effective focal length of 78.5 millimeters. Each contour has a radial width 178 of 0.125 millimeter. The above-described contour pattern is repeated 18 times over the entire radial 9-millimeter distance of multifocal fixation lens 114. To reduce undesirable reflections, the axis of multifocal fixation lens 114 is tilted at about a 2-degree angle relative to optical axis 110.

The effective focal length f' of each contour is calculated employing the equation:

$$f'=(f_{NOMINAL}(f_{CORECT}-d))/(f_{CORRECT}-f_{NOMINAL}),$$

where $f_{NOMINAL}$ is the distance between multifocal lens 114 and pinhole 108, $f_{CORRECT}$ is the focal length of a correction lens required by a user to produce fully corrected vision, and d is the distance between the pupil 28 of the user to multifocal lens 114.

The integration into scanner disk 116 of multifocal fixation lens 114, aspheric Fresnel lens 124, and Fresnel prism 122 eliminates the requirement for most optical components associated with the prior art scanner shown in FIG. 3. Because the optical components of scanner disk 116 are molded from a carefully machined die, they are inherently aligned and require no subsequent adjustments.

The focusing function of multifocal fixation lens 114 is described with reference to FIGS. 9A and 9B. It is customary to provide a method for focusing optical instruments to accommodate individuals having a wide range of visual acuity. A focus range of nominal +3 diopters to nominal −6 diopters is usually satisfactory. It is not necessary for the focusing range to be continuous, because most individuals have a ±1.5 diopter focal accommodation. Therefore, an adequate optical system employs multifocal fixation lens 114 that has four focal-length steps of nominal +3, nominal, nominal −3, and nominal −6 diopters.

Radial width 178 is preferably equal to or less than one-eighth of the minimum diameter of pupil 28 such that eye 5 (FIG. 1) simultaneously samples all four focal-lengths of multifocal fixation lens 114. The minimum diameter of pupil 28 is approximately 2 millimeters; therefore, the maximum radial width 178 is approximately 0.25 millimeter. The 0.125 millimeter preferred radial width is one-half the maximum width. Of course, a smaller radial width is desirable but is limited by Fresnel lens molding capabilities.

Figure 9A:
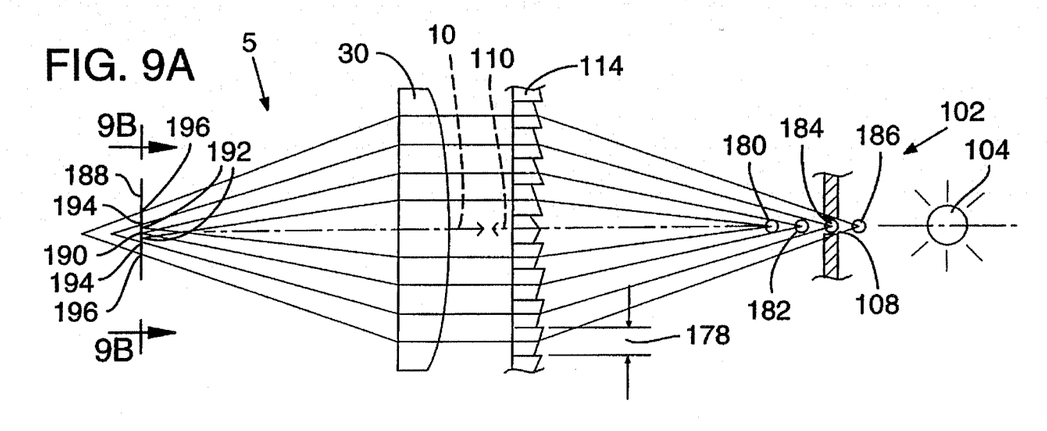
FIG. 9A is a schematic pictorial ray trace diagram illustrating the focal properties of the multifocal fixation lens of FIG. 8 when it is aligned with the visual axis of a human eye.

Referring to FIG. 9A, pinhole 108 of fixation target 102 generates a "single reticle" (illuminated pinhole). Multifocal fixation lens 114 creates a series of virtual images 180, 182, 184, and 186 of pinhole 108, one of which is focused on focal plane 188 by lens 30 of eye 5 irrespective of its particular visual acuity. Virtual image 184 corresponds to an in-focus image for an individual having nominal visual acuity. However, in the example shown, eye 5 is slightly "near-sighted" such that virtual image 182 is actually focused at point 190 on focal plane 188. Virtual images 180, 184, and 186 are imaged on focal plane 188 at respective points 192, 194, and 196.

Figure 9B:
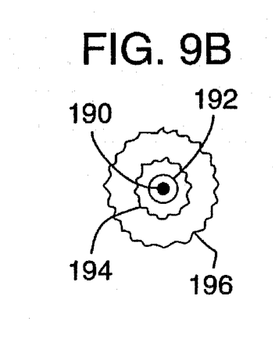
FIG. 9B is a schematic pictorial view of the image projected on a focal plane, such as in an eye, located at section line 9B—9B of FIG. 9A.

FIG. 9B depicts how virtual images 180, 182, 184, and 186 might appear to an individual looking through multifocal fixation lens 114 at fixation target 102. Eye 5 tends to focus on virtual image 182, the one which is most nearly in focus. What appears is point 190 against a background of successively more out-of-focus images of pinhole 108. The out-of-focus images appear as "circles of confusion" intersecting points 192, 194, and 196 on focal plane 188. When visual axis 10 of eye 5 is aligned with optical axis 110, point 190 and the circles of confusion are coaxial, thereby forming a familiar "bulls eye" shaped fixation target image that is simpler and less confusing than prior fixation targets that use multiple reticles or partly reflecting mirrors to create multiple virtual images at various focal distances.

The aligning function of multifocal fixation lens 114 is described with reference to FIGS. 10A, 10B, and 10C. In the example illustrated in FIG. 10A, visual axis 10 of eye 5 is misaligned with optical axis thereby focusing virtual image 182 at point 200 on focal plane 188. Virtual images 180, 184, and 186 are imaged on focal plane 188 at respective points 202, 204, and 206.

Figures 10A, 10C:
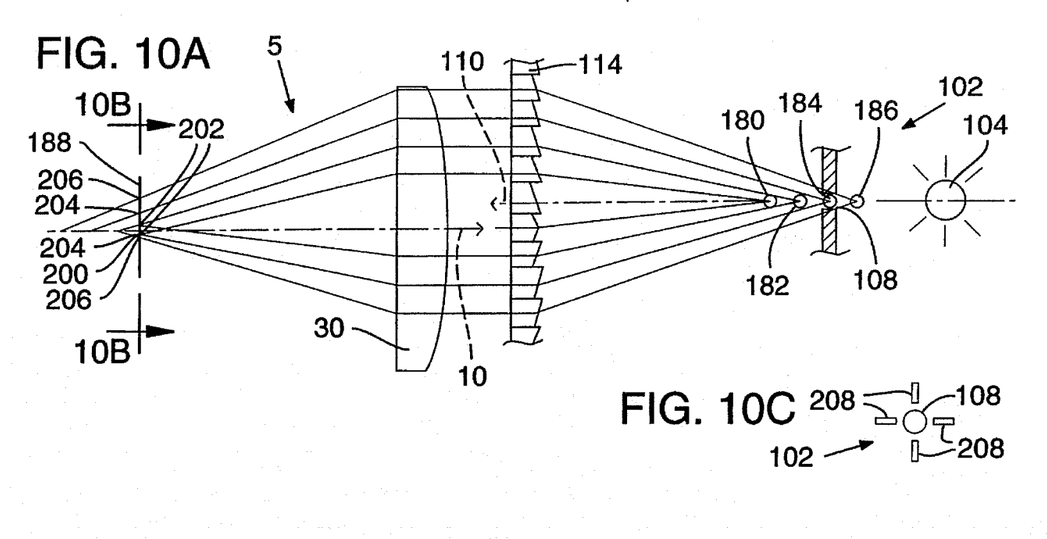
FIG. 10A is a schematic pictorial ray trace diagram illustrating the focal properties of the multifocal fixation lens of FIG. 8 when it is misaligned with the visual axis of a human eye.
FIG. 10C is an enlarged pictorial view of a preferred embodiment of a fixation target.
Figure 10B:
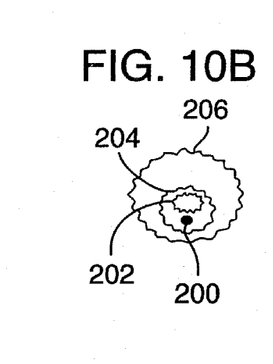
FIG. 10B is a schematic pictorial view of the image projected on the focal plane, such as in the eye, located at section line 10B—10B of FIG. 10A.

FIG. 10B represents how virtual images 180, 182, 184, and 186 might appear to an individual looking with axial misalignment through multifocal fixation lens 114 at fixation target 102. What appears is point 200 against a background of successively more out-of-focus images of pinhole 108. The out-of-focus images still appear as circles of confusion, but now intersect points 202, 204, and 206 on focal plane 188, thereby forming a non-concentric "bulls eye" shaped fixation target image that is clearly misaligned. The individual simply moves laterally relative to multifocal fixation lens 114 until the bulls eye image appears concentric, thereby aligning visual axis 10 with optical axis 110 as shown in FIG. 9A.

FIG. 10C shows a preferred embodiment of fixation target 102 that further improves the ability of a user to align visual axis 10 with optical axis 110. In this embodiment, four slits 208 are aligned radially with respect to pinhole 108 and spaced uniformly at 90 degree increments adjacent to the periphery of pinhole 108. Each of slits 208 are preferably shaped to have an open area about 10 percent or less than that of pinhole 108.

Two of slits 208 are arranged horizontally and two are arranged vertically to form a "cross hair" portion of fixation target 102 which, when combined with the existing "bulls eye" portion, enhances alignment of visual axis 10 with optical axis 110.

Skilled workers will recognize that portions of this invention my have alternative embodiments and that all embodiments may be used in applications in which the image is viewed by a camera or other imaging device rather than a human eye. In particular, multifocal fixation lens 114 is mounted on and rotates with scanner disk Scanner disk 116 need not, however, include either multifocal fixation lens 114 or IR filter 120, which may be located anywhere along the scanning beam path. Multifocal fixation lens 114 may have other than the above-described radial width and contour pattern and my have the pattern repeated in different orders, with different numbers of focal lengths, and/or with differing radial widths. Multifocal fixation lens 114 may also be other than a Fresnel lens, such as a rotating lens having multiple wedge-shaped portions each of a different focal length.

It will be obvious to those having skill in the art that many changes may be made to the details of the above-described embodiments of this invention without departing from the underlying principles thereof. Accordingly, it will be appreciated that this invention also applicable to optical scanning applications other than those found in eye fundus scanners. The scope of the present invention should, therefore, be determined only by the following claims.

We claim:

1. Apparatus for scanning a fundus of an eye and for detecting an ocular light pattern reflected by the fundus, comprising:

a source providing beams of visible and IR radiation directed substantially along a system optical axis;

a scanner disk positioned to rotate about the optical axis, the scanner disk including an optical scanner mounted at a location spaced apart from the optical axis and oriented to receive the IR radiation and direct a scanning beam into the eye from a plurality of angularly divergent positions onto the fundus at scanned points centered around the visual axis of the eye; and an angular encoder integral to the scanner disk, the plurality of angular divergent positions being determined by data received from the angular encoder.

2. The apparatus of claim 1 further including a fixation target illuminated by the source transmitting a fixation beam of the visible radiation through a multifocal lens that develops a series of virtual images of the fixation target that are spaced along the optical axis such that a visual axis of the eye can be aligned with the optical axis and substantially focused on at least one of the virtual images.

3. The apparatus of claim 2 further including a lenticular diffuser and in which the fixation target includes a pinhole that the source illuminates through the lenticular diffuser.

4. The apparatus of claim 3 in which fixation target further includes a set of slits arranged radially around a periphery of the pinhole.

5. The apparatus of claim 2 further including an IR filter positioned to block visible radiation present in the scanning beam.

6. The apparatus of claim 5 in which the filter is mounted adjacent to and facing the optical scanner on the scanner disk.

7. The apparatus of claim 1 in which the IR radiation reflects off the fundus and returns along a reciprocal path through the optical scanner, and in which the apparatus further includes a beam splitter that transmits the reflected IR radiation into a detector that generates data representing the intensity of the radiation reflected from the fundus at each scanned point.

8. The apparatus of claim 1 in which the optical scanner further includes a scanner prism mounted adjacent to and facing a scanner lens.

9. The apparatus of claim 8 in which at least one of the scanner lens and scanner prism is of a Fresnel type.

10. The apparatus of claim 1 further including a motor that is operatively connected to the scanner disk to rotate it at about six rotations per second.

11. The apparatus of claim 10 in which the scanner disk has a periphery and is suspended between at least two bearings and a capstan that is attached to the motor, the bearings and capstan being distributed around the periphery of the scanner disk.

12. The apparatus of claim 11 in which at least one of the bearings or the capstan is biased with a force directed toward the scanner disk.

13. The apparatus of claim 1 in which the angular encoder includes about 95 angular encoding positions and an index encoding position.

14. Apparatus for positioning a fundus of an eye for scanning and detecting an ocular light pattern reflected by the fundus, comprising:

a source providing beams of visible and IR radiation directed substantially along a system optical axis; and a fixation target illuminated by the source transmitting a fixation beam of the visible radiation through a multifocal lens that develops a series of virtual images of the fixation target that are spaced along the optical axis such that a visual axis of the eye can be aligned with the optical axis and substantially focused on at least one of the virtual images.

15. The apparatus of claim 14 further including a scanner disk positioned to rotate about the optical axis, the scanner disk including an optical scanner mounted at a location spaced apart from the optical axis and oriented to receive the IR radiation and direct a scanning beam into the eye from a plurality of angularly divergent positions onto the fundus at a substantially circular locus of scanned points centered around the visual axis of the eye.

16. The apparatus of claim 14 further including a lenticular diffuser and in which the fixation target includes a pinhole that the source illuminates through the lenticular diffuser.

17. The apparatus of claim 16 in which the fixation target further includes a set of slits arranged radially around a periphery of the pinhole.

18. The apparatus of claim 14 in which the multifocal lens is mounted to a scanner disk.

19. A method of scanning a fundus of an eye having a visual axis, comprising the steps of:

providing a source of visible and IR radiation directed substantially along a system optical axis;

illuminating a fixation target with the source;

positioning a scanner disk to rotate about the optical axis, the scanner disk including an optical scanner that is mounted at a location spaced apart from the optical axis and oriented to receive the IR radiation from the source and direct a scanning beam into the eye from a plurality of angularly divergent positions onto the fundus at scanned points centered around the visual axis of the eye;

mounting a multifocal lens on the scanner disk;

transmitting a fixation beam of the visible radiation through the multifocal lens to develop a series of virtual images of the fixation target that are spaced along the optical axis; and fixating the eye on the fixation target such that the visual axis is aligned with the optical axis and the eye is substantially focused on at least one of the virtual images.

20. The method of claim 19 further including the step of positioning an IR filter between the source and the eye to block visible radiation present in the scanning beam.

21. The method of claim 19 in which the IR radiation returns from the fundus along a reciprocal path through the optical scanner, the method further including the steps of:

positioning a beam splitter between the scanner lens and the source;

positioning a detector adjacent to the beam splitter; and transmitting the returned IR radiation by way of the beam splitter into the detector such that data are generated representing the intensity of the radiation returned from the fundus at each scanned point.

22. The method of claim 19 in which the optical scanner includes a scanner prism and a scanner lens, and the method further includes the step of positioning the scanner prism adjacent to and facing the scanner lens.

23. The method of claim 19 in which an angular encoder is operatively connected to the scanner disk, and the method further includes the step of determining the plurality of angular divergent positions by data received from the angular encoder.

24. The method of claim 23 further including the step of integrating the angular encoder into the scanner disk.

25. The method of claim 23 further including the step of providing the angular encoder with an index angle encoding position.

26. The method of claim 19 in which the scanner disk includes a periphery and is operatively rotated by a motor, and in which the positioning step further includes the step of suspending the scanner disk between at least two bearings and a capstan that is attached to the motor, the bearings and capstan being distributed around the periphery of the scanner disk.

27. A method of positioning a fundus of an eye having a visual axis for scanning by a beam of IR radiation, comprising the steps of:

providing a source of visible and IR radiation directed substantially along a system optical axis;

illuminating a fixation target with the source;

transmitting a fixation beam of the visible radiation through a multifocal lens that develops a series of virtual images of the fixation target that are spaced along the optical axis; and fixating the eye on the fixation target such that the visual axis is aligned with the optical axis and the eye is substantially focused on at least one of the virtual images.

28. The method of claim 27 further including the step of positioning a scanner disk to rotate about the optical axis, the scanner disk including an optical scanner that is mounted at a location spaced apart from the optical axis and oriented to receive the IR radiation from the source and direct a scanning beam into the eye from a plurality of angularly divergent positions onto the fundus at a substantially circular locus of scanned points centered around the visual axis of the eye.

29. Apparatus for focusing an image of an object through a lens onto a focal plane, the object, the lens, and the focal plane having substantially aligned axes, comprising:

a multifocal lens that simultaneously develops a series of virtual images of the object that are simultaneously spaced along the axes such that at least one of the virtual images is substantially focused on the focal plane.

30. The apparatus of claim 29 in which the lens and the focal plane are respectively the lens and fundus of an eye having impaired visual acuity, and in which at least one of the virtual images is focused on the fundus without the aid of an additional corrective lens.

31. Apparatus for scanning a fundus of an eye and for detecting an ocular light pattern reflected by the fundus, comprising:

a source providing beams of visible and IR radiation directed substantially along a system optical axis; and a scanner disk positioned to rotate about the optical axis, the scanner disk including an optical scanner mounted at a location spaced apart from the optical axis and oriented to receive the IR radiation and direct a scanning beam into the eye from a plurality of angularly divergent positions onto the fundus at scanned points centered around the visual axis of the eye, the optical scanner further including a scanner prism mounted adjacent to and facing a scanner lens, in which at least one of the scanner lens and the scanner prism is of a Fresnel type.

32. The apparatus of claim 31 further including a fixation target illuminated by the source transmitting a fixation beam of the visible radiation through a multifocal lens that develops a series of virtual images of the fixation target that are spaced along the optical axis such that a visual axis of the eye can be aligned with the optical axis and substantially focused on at least one of the virtual images.

33. The apparatus of claim 32 in which the fixation target includes a pinhole that is illuminated by the source.

34. The apparatus of claim 33 in which the fixation target further includes a set of slits arranged radially around a periphery of the pinhole.

35. The apparatus of claim 31 further including an IR filter positioned to block visible radiation present in the scanning beam.

36. The apparatus of claim 35 in which the IR filter is mounted adjacent to and facing the optical scanner on the scanner disk.

37. The apparatus of claim 31 in which the IR radiation reflects off the fundus and returns along a reciprocal path through the optical scanner, and in which the apparatus further includes a beam splitter that transmits the reflected IR radiation into a detector that generates data representing the intensity of the radiation reflected from the fundus at each scanned point.

38. The apparatus of claim 31 further including a motor that is operatively connected to the scanner disk to rotate it at about six rotations per second.

39. The apparatus of claim 38 in which the scanner disk has a periphery and is suspended between at least two bearings and a capstan that is attached to the motor, the bearings and capstan being distributed around the periphery of the scanner disk.

40. The apparatus of claim 39 in which at least one of the bearings or the capstan is biased with a force directed toward the scanner disk.

41. The apparatus of claim 31 further including an angular encoder that is operatively connected to the scanner disk, the plurality of angular divergent positions being determined by data received from the angular encoder.

42. The apparatus of claim 41 in which the angular encoder is integral to the scanner disk.

43. The apparatus of claim 42 in which the angular encoder includes about 95 angular encoding positions and an index encoding position.

44. Apparatus for positioning a fundus of an eye for scanning and detecting an ocular light pattern reflected by the fundus, comprising:

a source providing beams of visible and IR radiation directed substantially along a system optical axis; and a fixation target illuminated by the source transmitting a fixation beam of the visible radiation through a multifocal Fresnel lens that includes a series of radial contours that each provide a different predetermined effective focal-length, such that the multifocal Fresnel lens develops a series of virtual images of the fixation target that are spaced along the optical axis such that a visual axis of the eye can be aligned with the optical axis and substantially focused on at least one of the virtual images.

45. The apparatus of claim 44 further including a scanner disk positioned to rotate about the optical axis, the scanner disk including an optical scanner mounted at a location spaced apart from the optical axis and oriented to receive the IR radiation and direct a scanning beam into the eye from a plurality of angularly divergent positions onto the fundus at a substantially circular locus of scanned points centered around the visual axis of the eye.

46. The apparatus of claim 44 in which the fixation target includes a pinhole that the source illuminates.

47. The apparatus of claim 46 in which the fixation target further includes a set of slits arranged radially around a periphery of the pinhole.

48. The apparatus of claim 44 in which the multifocal lens is mounted to a scanning disk.

49. The apparatus of claim 44 in which the series of radial contours form a pattern that is repeated radially across a surface of the multifocal Fresnel lens.

50. The apparatus of claim 49 in which a number of contours in the series is four and the different predetermined effective focal-lengths include a nominal focal-length, a nominal focal-length plus about three diopters, a nominal focal-length minus about three diopters, and a nominal focal-length minus about six diopters.

51. The apparatus of claim 50 in which the nominal focal-length is about 72 millimeters.

52. A method of positioning a fundus of an eye having a visual axis for scanning by a beam of IR radiation, comprising the steps of:

providing a source of visible and IR radiation directed substantially along a system optical axis;

illuminating a fixation target with the source;

transmitting a fixation beam of the visible radiation through a Fresnel type multifocal lens including a series of molded radial contours each of which provides a different predetermined effective focal-length, the multifocal lens developing a series of virtual images of the fixation target that are spaced along the optical axis; and fixating the eye on the fixation target such that the visual axis is aligned with the optical axis and the eye is substantially focused on at least one of the virtual images.

53. The method of claim 52 further including the step of positioning a scanner disk to rotate about the optical axis, the scanner disk including an optical scanner that is mounted at a location spaced apart from the optical axis and oriented to receive the IR radiation from the source and direct a scanning beam into the eye from a plurality of angularly divergent positions onto the fundus at a substantially circular locus of scanned points centered around the visual axis of the eye.

54. The method of claim 52 in which the series of molded radial contours form a pattern that is repeated radially across a surface of the multifocal Fresnel lens.

55. Apparatus for focusing an image of an object through a lens onto a focal plane, the object, the lens, and the focal plane having substantially aligned axes, comprising a multifocal lens having radially repeating sets of four radial contours, each radial contour providing a different predetermined effective focal-length such that the multifocal lens develops a series of virtual images of the object that are spaced along the axes such that at least one of the virtual images is substantially focused on the focal plane, the different predetermined effective focal-lengths including a nominal focal-length, a nominal focal-length minus about three diopters, and a nominal focal-length minus about six diopters.

56. The apparatus of claim 55 in which the lens and the focal plane are respectively a lens and a fundus of a human eye having impaired visual acuity, and in which at least one of the virtual images is focused on the fundus without requiring an additional corrective lens.

57. The apparatus of claim 55 in which the nominal focal-length is about 72 millimeters.

58. Apparatus for focusing an image of an object through a lens of an eye having impaired visual acuity onto a fundus of the eye, the object, the lens, and the fundus having substantially aligned axes, comprising:

a multifocal lens that develops a series of virtual images of the object that are spaced along the axes such that at least one of the virtual images is substantially focused on the fundus of the eye without the aid of an additional corrective lens.

59. Apparatus for focusing an image of an object through a lens of an eye onto a fundus of the eye, the object, the lens, and the fundus having substantially aligned axes, comprising:

a multifocal lens that simultaneously develops a series of virtual images of the object that are simultaneously spaced along the axes such that at least one of the virtual images is substantially focused on the fundus.

* * * * *